United States Patent [19]

Francoeur et al.

[11] Patent Number: 4,959,365
[45] Date of Patent: Sep. 25, 1990

[54] TOPICAL COMPOSITIONS OF LIPOPHILIC PHARMACEUTICALS AGENTS

[75] Inventors: Michael L. Francoeur, Stonington; Russell O. Potts, Old Saybrook, both of Conn.

[73] Assignee: Pfizer Inc., New York, N.Y.

[21] Appl. No.: 340,112

[22] Filed: Apr. 18, 1989

Related U.S. Application Data

[63] Continuation-in-part of Ser. No. 161,926, Feb. 29, 1988, which is a continuation-in-part of Ser. No. 925,641, Oct. 31, 1986, abandoned.

[51] Int. Cl.$^5$ ............... A61K 31/535; A61K 31/505
[52] U.S. Cl. .................. 514/237.5; 540/485; 514/212; 514/269; 514/327; 514/863; 514/947; 544/159; 544/298; 546/221
[58] Field of Search ............ 544/159, 248, 298; 546/221; 540/485; 514/947, 237.5, 327, 212, 269, 863

[56] References Cited

U.S. PATENT DOCUMENTS

| | | | |
|---|---|---|---|
| 3,989,816 | 11/1976 | Rajadhyaksha | 424/60 |
| 4,316,893 | 2/1982 | Rajadhyaksha | 424/180 |
| 4,405,616 | 9/1983 | Rajadhyaksha | 424/244 |
| 4,444,762 | 4/1984 | Rajadhyaksha | 424/180 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,626,539 | 12/1986 | Aungst et al. | 514/282 |
| 4,711,888 | 12/1987 | Walker et al. | 514/269 |
| 4,764,379 | 8/1988 | Sanders et al. | 424/449 |
| 4,814,342 | 3/1989 | Hoover et al. | 514/385 |

FOREIGN PATENT DOCUMENTS 43738  1/1982  European Pat. Off. .
87/04706  8/1987  World Int. Prop. O. .

OTHER PUBLICATIONS

Skelly et al., Pharm., Res., V. 4., pp. 265-267 (1987).
Stoughton, Arch Dermatol., V. 118, pp. 474-477, (1982).
Cooper, J. Pharm. Sci., V. 73, pp. 1153-1156, (1984).
Patel et al., J. Soc. Cosmet. Chem., V. 36, pp. 303-311, (9185).
Akhter et al., J. Pharm. Pharmacol., V. 36, p. 7P (9184).
Cooper et al., J. Pharm. Sci., V. 74, pp. 688-689 (1985).
Priborsky et al., Drug Design Deliv., V. 2, pp. 91-97, (1987).
Bennett et al., J. Pharm. Pharmacol., V. 37, pp. 298-304, (1985).

*Primary Examiner*—Cecilia Shen
*Attorney, Agent, or Firm*—Peter C. Richardson; J. Trevor Lumb; Robert K. Blackwood

[57] ABSTRACT

Improved pharmaceutical compositions for the topical administration of a lipophilic, pharmaceutical agent to a human or lower animal subject comprising a safe and effective amount of a pharmaceutical agent, an aqueous solvent system comprising from about 15 to 75% by volume of one or more water miscible solvents, and a compound selected from certain 1-alkylazacycloheptan-2-ones and cis-olefin compounds of the formula

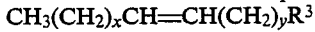

where $R^3$ is $CH_2OH$, $CH_2NH_2$ or $COR^4$ and $R^4$ is OH or $(C_1-C_4)$alkoxy, x and y are each an integer from 3 to 13 and the sum of x and y is from 10 to 16; and methods for treating disease in a human or lower animal by topical administration of such compositions.

28 Claims, No Drawings

TOPICAL COMPOSITIONS OF LIPOPHILIC PHARMACEUTICALS AGENTS

CROSS REFERENCE TO RELATED APPLICATIONS

This application is a continuation-in-part of co-pending application Ser. No. 161,926, filed Feb. 29, 1988, which is a continuation-in-part of patent application Ser. No. 925,641, filed Oct. 31, 1986, now abandoned.

BACKGROUND OF THE INVENTION

The invention relates to improved pharmaceutical compositions for topical administration to a human or lower animal subject and methods for their use in treatment of disease.

The following patents to Rajadhyaksha issued from 1976 to 1984 disclose methods and compositions employing 1-alkylazacycloheptan-2-ones and homologs thereof for enhanced penetration of pharmacologically active agents through human and animal skin;

U.S. 3,989,816; U.S. 4,316,893; U.S. 4,405,616 and 4,444,762.

Stoughton, Arch. Derm., 118, 474–477 (1982) relates to 1-dodecylazacycloheptan-2-one, referred to herein as Azone, and its ability to enhance percutaneous penetration.

Cooper, U.S. 4,557,934 and 4,537,776, discloses topical compositions of nonsteroidal antiinflammatory compounds, antiviral agents, antitussives and other drugs containing ethanol, certain glycols, pyrrolidone, 1-(2-hydroxyethyl)-aza-cyclopentan-2-one and from 1–35% 1-dodecylazacycloheptan-2-one (Azone).

Cooper, J. Pharm. Sci., 73, 1153–1156 (1984) discloses a method for increased transport of nonpolar molecules like salicylic acid through skin by adding fatty alcohols or fatty acids to transdermal formulations in various glycol solvents.

Akhter and Barry, J. Pharm. Pharmacol., 36, 7P (1984), report that oleic acid and Azone enhance dermal penetration of flurbiprofen formulations in propylene glycol and other solvents.

EP43738 discloses a binary dermal penetration enhancing vehicle for antiinflammatory agents containing a $C_3$—$C_4$-diol, diol ester or diol ether and a cell envelope-disordering compound selected from, inter alia, the lower alkyl esters of $C_{12}$–$C_{14}$ fatty acids, oleic acid, lauryl acetate and myristyl acetate.

Patel, et al., Journ. Soc. Cosmetic Chem. 36, 303–311 (1985) has noted that propylene glycol, a common constituent of prior art pharmaceutical formulations for transdermal use, causes irritation and/or sensitization when its concentration exceeds ten percent.

Walker et al., U.S. 4,711,888 disclose certain pyrimidine derivatives, including 5-hydroxy-4,6-dimethyl-2-(6-phenylhexyl)aminopyrimidine of the formula

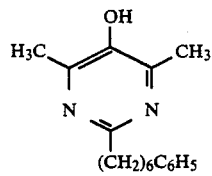

(I)

which inhibit leukotriene synthesis and so are useful in the treatment of certain pulmonary inflammatory, allergic, gastrointestinal, cardiovascular and dermatological diseases such as psoriasis.

Hoover et al., U.S. 4,814,342 disclose certain peptides, including compounds of the formula

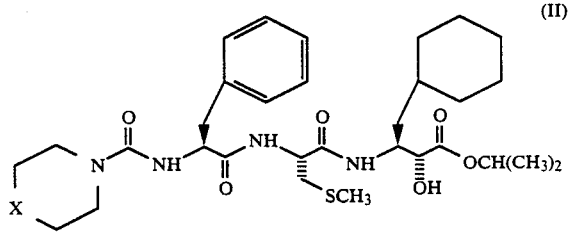

(II)

wherein X is O or C=O, there named, respectively, N-morpholinocarbonyl-L-phenylalanine-S-methyl-L-cysteine-norcyclostatine isopropyl ester or simply morpholinocarbonylPhe S-MeCysnor-C-Sta isopropyl ester, and N-(4-oxopiperidino)carbonyl-L-phenylalanine-S-methyl-L-cysteine-norcyclostatine isopropyl ester or simply 4-oxopiperidinocarbonylPhe S-MeCysnor-C-Sta isopropyl ester. These compounds inhibit the angiotensinogen-cleaving action of the enzyme renin and so are useful as antihypertensive agents.

In our prior applications, cited above, we generally disclose transdermal flux enhancing pharmaceutical compositions comprising a pharmaceutical agent, a solvent comprising water and a near optional level of a water miscible solvent and a penetration enhancing compound which is a 1-alkylazacycloheptan-2-one or a cis-olefinic fatty acid, ester, alcohol or amine. The specific pharmaceutical agents disclosed in these earlier applications, (e.g., salicylic acid, ubuprofen, glipizide, piroxicam) are generally hydrophilic (lipophobic).

It is known that hydrophobic (lipophilic) drugs containing readily metabolized groups, (e.g., polypeptides, and certain pyrimidine drugs proposed for topical use) are particular prone to metabolism intradermally and in other skin-like biomembranes, such as mucous membrane. See, for example, Tauber in "Transdermal Drug Delivery", Hadgraft and Guy, eds., Marcel Dekker, Inc., (New York) pp. 99–112; Banga et al., Intl. J. Pharmaceutics, v. 48, pp. 15–50 (1988). Surprisingly, we have now found that the lipophilic drugs in this type of formulation are not only better carried across these barriers, offering advantageous routes (e.g., transdermally) for maximal systemic delivery of certain readily metabolized lipophilic drugs (such as the renin inhibitors of the formula II above); but metabolism of these drugs within the biomembrane is inhibited and high intramembrane (e.g. intradermal) levels of such drugs can be achieved, particularly valuable where the site of action is in the skin (such as in the case of psoriasis) or in another such biomembrane (e.g., nasal, rectal, ophthalmic, buccal, etc.). Indeed, the present invention is also of value in oral, intramuscular or subcutaneous routes of administration when there is significant metabolism of a lipophilic drug at these alternative sites of absorption, e.g., in the lumen of the gut.

SUMMARY OF THE INVENTION

In its preferred form, the present invention is directed to a pharmaceutical composition for topical administration of a lipophilic, pharmaceutical agent to a human or lower animal subject comprising (a) a safe and effective amount of said agent;

(b) a solvent system comprising water and from about 15 to 75% by volume of one or more water miscible solvents, and (c) from about 0.01 to 5% (w/v) of a compound which is a 1-alkylazacycloheptan-2-one, said alkyl having from 8 to 16 carbon atoms, or a cis-olefin cf the formula

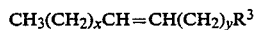

where $R^3$ is $CH_2OH$, $CH_2NH_2$ or $COR$ ($C_1$–$C_4$)alkoxy, x and y are each an integer from 3 to 13 and the sum of x and y is from 10 to 16.

A further surprising feature of the invention resides in the fact that for a given pharmacologically active compound there appears to be a certain concentration of solvent(s) within the above range at which the flux across the topical barrier is optimal, and that the solvent system employed must be aqueous. The particularly preferred composition of the invention is one in which the concentration of the solvent or solvents is within 10% of the concentration which gives optimum flux across the biomembrane and/or maximum intramembrane (e.g., intradermal) levels of active drug for that particular pharmaceutical agent. While the entire range of about 15 to 75% for the concentration of the solvent or combined solvents, ordinarily gives markedly improved flux or drug level in comparison with solvent levels outside that range, the more limited range is a "window" within which flux or drug level is found to be most beneficial.

The aqueous solvent system of the invention comprises water and one or more water miscible solvents. Such water miscible solvents include, but are not limited to, methanol, ethanol, isopropyl alcohol, propylene glycol, polyethylene glycol and glycerin. Preferred solvents for this invention are those that are least damaging to skin and include ethanol and glycerin. A particularly preferred solvent of this invention is ethanol. The water used in this invention may be buffered and the pH adjusted to optimize stability of the particular pharmaceutical agent and to reduce or eliminate damage to skin. If the water is buffered, it is preferred that the water be buffered to about pH 6.5 to pH 7.5. Anionic buffers are preferable for such purpose. An appropriate pharmaceutically acceptable anionic buffer is Sorensen's Buffer which comprises $NaH_2PO_4.H_2O$, $Na_2HPO4$ and NaCl and which is well known to those skilled in the art. Certain cationic buffers such as Tris also can be employed but it has been found that Tris reduces the effect of oleic acid on stratum corneum lipids in a concentration dependent manner.

The ratio of water to solvent or solvents for optimum flux or membrane drug level will vary to some extent as a function of the solvent(s), the enhancer compound and the pharmaceutical agent of the particular composition. The range of ratios for water/solvent(s) within the scope of this invention is from about 15/85 (% v/v) to about 85/15 (% v/v).

While the present invention is useful for compositions containing a wide variety of lipophilic pharmaceutical agents, either in the form of the pharmacologically active compounds per se or in the form of a prodrug, it is especially useful for compositions used in treatment of humans or lower animals suffering from psoriasis or hyptertension.

Especially useful pharmaceutical agents in the present invention are the lipophilic pyrimidines of above cited Walker et al., particularly the compound of the formula (I) above, and the pharmaceutically acceptable salts thereof; and the lipophilic peptide derivatives of above cited Hoover et al., particularly the compounds of the formula (II) above. The preferred salt of the compound of the formula (I) is the 1:1 salt with phosphoric acid.

A particularly preferred class of compounds as useful enhancers in the present invention are the cis-monoenoic acids of the formula

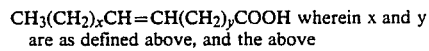 wherein x and y are as defined above, and the above 1-alkylazacycloheptan-2-ones wherein said alkyl has from 10 to 14 carbon atoms. Especially preferred members within this class of penetration enhancers are cis-9-tetradecenenoic acid, cis-6-pentadecenoic acid, cis-6-hexadecenoic acid, cis-9-hexadecenoic acid, cis-9-octadecenoic acid (oleic acid), cis-6octadecenoic 12-octadecenoic acid, cis-5-eicosenoic, cis-9eicosenoic acid, cis-11-eicosenoic acid, cis-14eicosenoic acid, 1-decylazacycloheptan-2-one, 1-dodecylazacycloheptan-2-one and 1-tetradecylaza-cycloheptan-2-one. Most particularly preferred, because of its efficacy and ease of availability is cis-9-octadecenoic acid (oleic acid).

A preferred range of concentration of water miscible solvent or combined water miscible solvents for providing optimum flux across the biomembrane or intramembrane drug levels of lipophilic pharmaceutical agents in the present compositions is from 20 to 60% by volume.

A particularly preferred range of concentration for the enhancer compounds of the present invention is from 0.1 to 1% w/v and especially from 0.25 to 0.5% w/v for reasons of efficiency and lack of irritation.

As mentioned above, the invention also provides methods of treating diseases in man or lower animals by employing the pharmaceutical compositions of the present invention.

DETAILED DESCRIPTION OF THE INVENTION

A safe and effective amount of a pharmaceutical agent for use in the pharmaceutical compositions of the present invention is understood herein to mean an amount that will provide therapeutically useful blood and/or local (e.g., dermal) levels of the active compound by the topical route of administration. The therapeutically useful levels for the individual pharmacologically active compounds and prodrugs are those known in the art to be useful for each of such compounds. Said pharmaceutical compositions can assume a variety of forms, e.g., a solution, gel or suspension of the active compound or prodrug When the pharmaceutical agent is a prodrug of a physiologically active compound, it is generally a structurally related compound or derivative of an active compound which is absorbed into the human or lower animal body where it is converted to the desired physiologically active compound. The prodrug itself may have little or none of the desired activity.

Within the scope of sound medical judgment the amount of a given pharmaceutical agent used will vary with the particular condition being treated, the severity of the condition, the duration of the treatment, the nature of the compound employed, the condition of the patient and other factors within the specific knowledge and expertise of the attending physician.

Dosage forms for the pharmaceutical compositions of the invention may include solutions, lotions, ointments, creams, gels, suppositories, rate-limiting sustained release formulations and devices therefor.

In addition to the requisite pharmaceutical agent, solvent(s), water and enhancing compound for the compositions of the invention, typical dosage forms can include inert carriers such as gel-producing materials, mineral oil, emulsifying agents, benzyl alcohol and the like.

The present invention is illustrated by the following examples. However, it should be understood that the invention is not limited to the specific details of these examples.

EXAMPLE 1

Skin Samples for Penetration Studies

Murine skin was prepared from male, hairless mice, 8 to 16 weeks of age. The mice were sacrificed by cervical dislocation and a section of full-thickness abdominal skin was surgically excised and mounted between two identical diffusion half-cells (Crown Glass Co., Somerville, N.J.) having 1.0 cm$^2$ surface area. The skins were then hydrated for about 18 hours with Sorensen's isotonic buffer (0.067M sodium phosphate, pH 7.38) prior to conducting experiments.

Human skin, taken in surgery or autopsy, was dermatoned to about 400 micrometers ($\mu$m) thickness and hydrated in the same manner.

Stratum corneum sheets were prepared from porcine or human skin by trypsin treatment. Thus, full thickness skin samples were dermatomed to a thickness of 350–400 $\mu$m, spread, stratum corneum side up, on filter paper saturated with 0.5% crude trypsin (Type II, sigma Chemical, St. Louis, Mo.) in phosphate buffered saline, pH 7.4. After several hours at 37° C., the stratum corneum layer was peeled away from underlying layers, washed in soybean trypsin inhibitor and several changes of distilled water and spread on wire mesh to dry. Samples were stored desiccated at room temperature until used.

EXAMPLE 2

Permeability of MorpholinocarbonylPhe S—MeCysnor—C—Sta Isopropyl Ester (I, X=0) Across Murine Skin from 0.01M H$_3$PO$_4$/Ethanol Solutions of ethanol in 0.01M H$_3$PO$_4$ (0%, 20%, 40%, 50%) were prepared with or without 0.25% oleic acid. The amount of drug used was based on the solubility of the drug in each solution at saturation concentration. Permeation studies were done with murine skin. The receiver side of the diffusion cell was filled with Sorensen buffer, pH 7.4 and the donor side contained the drug in various ethanol solutions. In the experiment, 200 $\mu$l of the receiver solution was sampled at different time intervals. 100 $\mu$l of this solution was counted in the scintillation counter and the remaining 100 $\mu$l was diluted with equivalent amount of methanol to be used in the HPLC instrument.

Results of the diffusion experiments showed maximal flux from the vehicle with 50% ethanol and 0.25% oleic acid (Table I).

TABLE I

Effect of Ethanol Concentration and Oleic Acid on the Flux of MorpholinocarbonylPhe S-MeCysnor-C-Sta Isopropyl Ester in 0.01M H$_3$PO$_4$ Across Murine Skin

| % EtOH | Drug Conc. (mg/ml) | % Oleic Acid | Flux × 10$^8$ mol/cm$^2$/hr | KP × 10$^3$ (cm/hr) |
|---|---|---|---|---|
| 0 | 0.2 | 0 | 0.024 | 0.75 |
|   |   | 0.25 | 0.07 | 2.18 |
| 20 | 0.3 | 0 | 0.095 | 1.97 |
|   |   | 0.25 | 0.08 | 1.07 |
| 40 | 2.6 | 0 | 0.177 | 0.42 |
|   |   | 0.25 | 0.59 | 1.4 |
| 50 | 11.4 | 0 | 0.46 | 0.25 |
|   |   | 0.25 | 2.78 | 1.50 |

EXAMPLE 3

Permeability of MorpholinocarbonylPhe S-MeCysnor-C-Sta Isopropyl Ester (I, X=CO) Across Porcine and Human Skin Dermatomed porcine and human skins were mounted between the chambers of the diffusion cells. The donor chamber contained the radiolabeled drug in 50% EtOH—.01M H$_3$PO$_4$ with or without 0.25% oleic acid. The receiver contained Sorensen buffer, pH 7.4. A number of cells were set up to allow sampling for both diffusion and HPLC studies. The receiver side was sampled at different time points for the diffusion studies and sampled once at the end of the experiment for HPLC studies. The fluxes through porcine and human skin were lower than murine skin. The incorporation of 0.25% oleic acid however, greatly increased the permeation of the test compounds through both skins (Table II).

TABLE II

Effect of Oleic Acid on the Flux of MorpholinocarbonylPheS-MeCysnor-C-Sta Isopropyl Ester in 50% Ethanol-0.01M H$_3$PO$_4$ Across Skin

| Skin | % Oleic Acid | Flux × 10$^8$ (mol/cm$^2$/hr) | KP × 10$^3$ (cm/hr) |
|---|---|---|---|
| Murine | 0 | 0.46 | 0.25 |
|  | 0.25 | 2.78 | 1.5 |
| Porcine | 0 | 0.034 | 0.019 |
|  | 0.25 | 0.35 | 0.19 |
| Human | 0 | 0.008 | 0.0045 |
|  | 0.25 | 0.075 | 0.041 |

EXAMPLE 4

Concentrations of Unmetabolized Drug in the Receiver Chamber in Skin in Examples 2 and 3

The content of the receiver of the diffusion cell was taken at the time when the radioactive counts were high enough to be injected into the HPLC system. These samples were diluted with equal volume of methanol to stop the degradation of the drug by the enzymes eluted from the skin. In the case of human skin, only the receiver samples from vehicles with oleic acid were used. To increase the radioactive count, the receiver content at the end of 85 hours was evaporated to dryness and reconstituted with 200 $\mu$l of the mobile phase used in the HPLC system (45% acetonitrile-55% 0.1M KH$_2$PO$_4$, pH 2.3). In the case of porcine and murine skin, the radioactive counts of the receiver were sufficiently high at the end of 48 and 70 hours that no further concentration of the samples was necessary.

The mounted porcine and human skin skins were rinsed twice with Sorensen buffer and stored by freezing in liquid nitrogen. To determine the drug level in the skin, the samples were thawed, the area through which the drug has permeated was punched out and treated with ethyl acetate for a few days to allow the drug to elute into the solvent. The solvent was evaporated to dryness and the residue taken up in the HPLC mobile phase.

The fractions collected using the HPLC technique show the amount of intact drug in the receiver and in the skin. In the experiments with murine skin only the receiver sample from the vehicle containing oleic acid was analyzed. It contained 90% of the intact drug (Table III).

In the porcine skin experiments, the receiver and skin samples from vehicles with and without oleic acid were both analyzed. The intact drug from the receiver averaged to about 23% from vehicle without oleic acid and 67% from vehicle with oleic acid. The intact drug from the skin averaged to about 97% from vehicles with oleic acid. However, the results from the vehicle without oleic acid were unreliable due to the discrepancy and low magnitude in the counts.

In the experiments with human skin, the skin samples from the vehicles with or without oleic acid and the receiver sample from the vehicle with oleic acid were analyzed. Only 20% of the intact drug was found in the receiver sample probably due to the rapid degradation of CP-80,794 by the enzymes of the skin. The intact drug in the skin from the vehicle without oleic acid was 55% and 98% from the vehicle with oleic acid (Table IV).

Overall, the presence of oleic acid in the vehicle increased the elution of intact drug.

TABLE III

HPLC Analysis of MorpholinocarbonylPhe S-MeCysnor-C-Sta Isopropyl Ester Permeated into Mouse Skin

| Elution Time (minutes) | Std. 3H DPM | 50% EtOH/ 0.25% Oleic Acid Receiver |
|---|---|---|
| 0.5 | 36.10 | 23.30 |
| 1.0 | 0.00 | 0.00 |
| 1.5 | 0.00 | 0.00 |
| 2.0 | 492.00 | 44.60 |
| 2.5 | 195.14 | 114.50 |
| 3.0 | 47.05 | 49.46 |
| 3.5 | 97.43 | 86.02 |
| 4.0 | 134.00 | 241.92 |
| 4.5 | 63.49 | 120.20 |
| 5.0 | 31.69 | 22.38 |
| 5.5 | 119.22 | 0.00 |
| 6.0 | 127.08 | 0.79 |
| 6.5 | 57.48 | 33.70 |
| 7.0 | 41.05 | 17.12 |
| 7.5 | 30.23 | 0.00 |
| 8.0 | 35.22 | 0.00 |
| 8.5 | 1211.35 | 0.00 |
| 9.0 | 23178.00 | 173.60 |
| 9.5 | 23576.30 | 4578.05 |
| 10.0 | 7523.06 | 2265.06 |
| 10.5 | 3719.66 | 662.30 |
| 11.0 | 497.01 | 227.12 |
| 11.5 | 293.37 | 114.31 |
| 12.0 | 0.00 | 55.90 |
| Total DPM of Drug Eluted: | 61505.93 | 8830.33 |
| Intact Drug Eluted | 58787.40 | 8020.44 |
| % Intact Drug Eluted | 95.58 | 90.82 |
| % Recovery | 116.02 | 106.54 |

TABLE IV

HPLC Analysis of MorpholinocarbonylPhe S-MeCysnor-C-Sta Isopropyl Ester Permeated into Human Skin

| Elution Time (minutes) | Std. 3H DPM 1 | Std. 3H DPM 2 | 50% EtOH Receiver 0.25% Oleic Acid | 50% EtOH Skin 0.25% Oleic Acid | 50% EtOH Skin No Oleic Acid |
|---|---|---|---|---|---|
| 0.5 | 62.60 | 71.62 | 21.98 | 0.00 | 9.78 |
| 1.0 | 0.00 | 3.77 | 4.89 | 23.53 | 3.67 |
| 1.5 | 0.00 | 0.00 | 2264.16 | 38.20 | 1.22 |
| 2.0 | 12.48 | 7.71 | 634.45 | 10.49 | 0.00 |
| 2.5 | 3.65 | 0.00 | 43.33 | 82.43 | 5.92 |
| 3.0 | 2.40 | 10.21 | 16.60 | 31.63 | 3.64 |
| 3.5 | 48.61 | 56.19 | 130.73 | 122.35 | 260.44 |
| 4.0 | 8.67 | 32.81 | 16.90 | 30.35 | 2.48 |
| 4.5 | 0.00 | 0.00 | 0.00 | 7.88 | 0.00 |
| 5.0 | 21.92 | 0.00 | 6.43 | 55.36 | 2.46 |
| 5.5 | 6.25 | 25.27 | 1.31 | 100.12 | 4.96 |
| 6.0 | 4.92 | 0.00 | 5.24 | 5.30 | 0.00 |
| 6.5 | 2.53 | 0.00 | 2.59 | 13.11 | 0.00 |
| 7.0 | 6.27 | 2.56 | 1.29 | 0.00 | 0.00 |
| 7.5 | 12.63 | 0.00 | 0.00 | 17.01 | 0.00 |
| 8.0 | 3594.97 | 0.00 | 8.79 | 533.22 | 137.44 |
| 8.5 | 3071.75 | 2130.92 | 700.37 | 27206.80 | 234.98 |
| 9.0 | 69.53 | 4286.06 | 110.55 | 1281.52 | 3.77 |
| 9.5 | 4.96 | 73.50 | 5.07 | 99.35 | 2.49 |
| 10.0 | 6.11 | 29.15 | 1.26 | 38.09 | 0.00 |
| 10.5 | 0.00 | 8.95 | 6.51 | 18.47 | 0.00 |
| 11.0 | 7.51 | 0.00 | 0.00 | 1.29 | 0.00 |
| 11.5 | 0.00 | 0.00 | 0.00 | 0.00 | 4.94 |
| 12.0 | 0.00 | 0.00 | 0.00 | 3.86 | 3.79 |
| Total DPM of Drug Eluted | 6947.70 | 6738.72 | 3982.44 | 29720.36 | 681.98 |
| Intact Drug Eluted | 6747.32 | 6519.63 | 826.04 | 29158.98 | 378.68 |
| % Intact Drug Eluted | 97.12 | 96.75 | 20.74 | 98.11 | 55.53 |
| % Recovery | 108.92 | 105.64 | 90.21 | 110.42 | 28.44 |

EXAMPLE 5

Permeability and Metabolism of 5-hydroxy-4,6 dimethyl-2-6-(phenylhexyl)aminopyrimidine 1:1 Salt with Phosphoric Acid in Mouse Skin By the methods of the preceding Examples, with flux across murine skin being determined over a 24 hour period in a standard diffusion cell using 0.05 mg/ml of 5-hydroxy-4,6-dimethyl-2-(6-phenylhexyl-)aminopyrimidine in the form of its 1:1 phosphoric acid salt in 50% ethanol, with and without 0.25% of oleic acid. Results are shown in Table V.

The presence of 0.25% oleic acid in the formulation enhanced the flux approximately 10 fold. Interestingly, the concentration of drug within the skin was enhanced 30 fold in the presence of oleic acid. It is evident that flux enhancement does not correlate directly with drug content within the skin.

Further differences were seen when receiver fluid was analyzed by HPLC. Two increasingly polar metabolites were seen in the receiver fluid (metabolite A and B, respectively) with no detectable amount of intact drug seen with the low formulation without oleic acid. However, when oleic acid was present, there were marked changes in the metabolite profile. First, a relatively large amount of drug was found in the receiver compartment. Second, the relative proportion of the two polar metabolites was reversed, with the least polar of the two dominating.

TABLE V

Permeability of 5-Hydroxy-4,6-dimethyl-2-6-(phenylhexyl)aminopyrimidine 1.1 Salt with Phosphoric Acid in Mouse Skin

| Vehicle | Experiment No. | Flux (mol/cm²/hr) | Skin Conc. (μM) |
|---|---|---|---|
| 1:1 EtOH:H$_2$O | 1 | $1.47 \times 10^{-11}$ | 60 |
|  | 2 | $2.13 \times 10^{-11}$ | 114 |
| 1:1 EtOH:H$_2$O with 0.25% oleic acid | 1 | $2.59 \times 10^{-10}$ | 3812 |
|  | 2 | $4.31 \times 10^{-10}$ | 3812 |

We claim:

1. A pharmaceutical composition for the topical treatment of psoriasis or hypertension in a human or lower animal which comprises
    (a) a safe and effective amount of a lipophilic pharmaceutical agent; wherein for the treatment of psoriasis the agent is 5-hydroxy-b 4,5-dimethyl-2-(6-phenylhexyl)aminopyrimidine or a pharmaceutically acceptable acid addition salt thereof; and for the treatment of hypertension the agent is compound of the formula

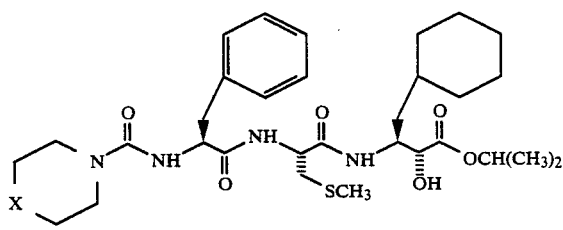

where X is O or C=O;
    (b) a solvent system comprising water and from about 15 to 75% by volume of one or more water miscible solvents selected from the group consisting of methanol, ethanol and isopropyl alcohol; and
    (c) from about 0.01 to 5% (w/v) of a compound which is a 1-alkylazacycloheptan-b 2-one, said alkyl having from 8 to 16 carbon atoms, or a cis-olefin of the formula

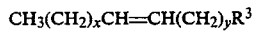

where R$^3$ is CH$_2$OH, CH$_2$NH$_2$ or COR, and R$^4$ is OH or (C$_1$-C$_4$)alkoxy, x and y are each an integer from 3 to 13 and the sum of x and y is from 10 to 16;
    wherein in said solvent system said water miscible solvent content is within 10% of that which gives optimal flux across the topical biomembrane and/or maximal intramembrane levels for said agent.

2. A composition according to claim 1 wherein the compound is cis-9-tetradecenoic acid, cis-6-pentadecenoic acid, cis-6hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

3. A composition according to claim 2 wherein the compound is cis-9-octadecenoic acid (oleic acid).

4. A composition according to claim 3 wherein the water miscible solvent is ethanol.

5. A composition according to claim 1 wherein the agent is 5-hydroxy-4,6-dimethyl-2-(6-phenylhexyl)aminopyrimidine or a pharmaceutically acceptable acid addition salt thereof.

6. A composition according to claim 5 wherein the compound is cis-9-tetradecenoic acid, cis-6-pentadecenoic acid, cis-6hexadecenoic acid, cis-9-hexadecenoic acid, cis-9-octadecenoic acid (oleic acid), cis-6octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

7. A composition according to claim 6 wherein the compound is cis-9-octadecenoic acid (oleic acid).

8. A composition according to claim 7 wherein the water miscible solvent is ethanol.

9. A composition according to claim 1 wherein the agent is

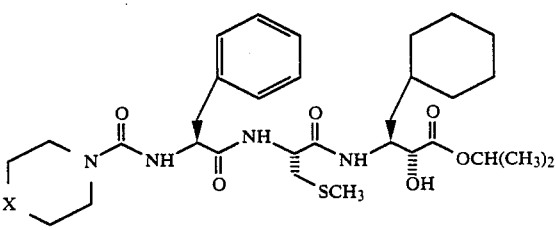

where X is 0 or C=0.

10. A composition according to claim 13 wherein X is 0.

11. A composition according to claim 14 wherein X is C=O.

12. A composition according to claim 13 wherein the compound is cis-9-tetradecenoic acid, cis-6-pentadecenoic acid, cis-6-hexadecenoic acid, cis-9hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

13. A composition according to claim 12 wherein the compound is cis-9-octadecenoic acid (oleic acid). hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

14. A composition according to claim 13 wherein the water miscible solvent is ethanol.

15. A method of treating psoriasis or hypertension in a human or lower animal which comprises topical administration f a psoriasis alleviating or antihypertensive amount of a pharmaceutical composition of claim 1.

16. A method according to claim 15 wherein the compound is cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

17. A method according to claim 16 wherein the compound is cis-9-octadecenoic acid (oleic acid).

18. A method according to claim 17 wherein the water miscible solvent is ethanol.

19. A method according to claim 15 wherein the agent is 3-hydroxy-4,6-dimethyl-2-(6-phenylhexyl-)aminopyridimidine or a pyrimidine or a pharmaceutically acceptable acid addition salt thereof.

20. A method according to claim 19 wherein the compound is cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacyclo-heptan-2-one.

21. A method according to claim 20 wherein the compound is cis-9-octadecenoic acid (oleic acid).

22. A method according to claim 21 wherein the water miscible solvent is ethanol.

23. A method according to claim 15 wherein the agent is

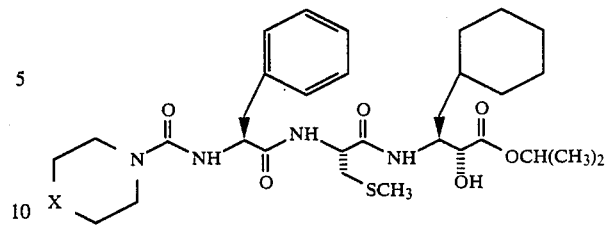

where X is 0 or C=0.

24. A method according to claim 23 wherein X is 0.

25. A method according to claim 34 wherein X is C=0.

26. A method according to claim 23 wherein the compound is cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-ocatadecenoic acid, cis-5-eicosenoic, cis-9-eicosenoic acid, cis-11-eicosenoic acid, cis-14-eicosenoic acid, 1-decylazacycloheptan-2-one, 1-dodecylazacyclopheptan-2-one or 1-tetardecylazacyclheptan-2-one.

27. A method according to claim 26 wherein the compound is cis-9-octadecenoic acid (oleic acid).

28. A method according to claim 27 wherein the water miscible solvent is ethanol.

* * * * *